(12) United States Patent
Klok et al.

(10) Patent No.: US 11,339,411 B2
(45) Date of Patent: May 24, 2022

(54) PROCESS TO PREPARE ELEMENTAL SULPHUR

(71) Applicant: Paqell B.V., Utrecht (NL)

(72) Inventors: Johannes Bernardus Maria Klok, Rhenen (NL); Annemiek Ter Heijne, Rhenen (NL); Frederikus De Rink, Amersfoort (NL); Cees Jan Nico Buisman, Harich (NL)

(73) Assignee: Paqell B.V., Utrecht (NL)

( * ) Notice: Subject to any disclaimer, the term of this patent is extended or adjusted under 35 U.S.C. 154(b) by 0 days.

(21) Appl. No.: 16/616,636

(22) PCT Filed: May 30, 2018

(86) PCT No.: PCT/EP2018/064150
§ 371 (c)(1),
(2) Date: Nov. 25, 2019

(87) PCT Pub. No.: WO2018/219990
PCT Pub. Date: Dec. 6, 2018

(65) Prior Publication Data
US 2020/0095610 A1    Mar. 26, 2020

(30) Foreign Application Priority Data

Jun. 1, 2017   (EP) .................................. 17173887

(51) Int. Cl.
*C12P 3/00* (2006.01)
*B01D 53/52* (2006.01)
(Continued)

(52) U.S. Cl.
CPC ............... *C12P 3/00* (2013.01); *B01D 53/52* (2013.01); *B01D 53/84* (2013.01); *B01D 53/965* (2013.01);
(Continued)

(58) Field of Classification Search
CPC ........... C12P 3/00; B01D 53/84; B01D 53/52; B01D 53/965; C25B 1/00; C10L 3/103;
(Continued)

(56) References Cited

U.S. PATENT DOCUMENTS

2011/0011799 A1    1/2011 Rozendal et al.

FOREIGN PATENT DOCUMENTS

CN        105176614 A  *  12/2015
EP        0958251 B1    10/2002
(Continued)

OTHER PUBLICATIONS

Norris et al. Characteristics of *Sulfobacillus acidophilus* sp. nov. and other moderately thermophilic mineral-sulphide-oxidizing bacteria. Microbiology (1996), 142, 775-783; (Year: 1996).*
(Continued)

*Primary Examiner* — Sean C. Barron
(74) *Attorney, Agent, or Firm* — Nixon Peabody LLP; Ronald I. Eisenstein; Nicole D. Kling

(57) ABSTRACT

The invention is directed to a process to prepare elemental sulphur by (i) contacting an aqueous solution comprising bisulphide with oxidised sulphide-oxidising bacteria under anaerobic conditions wherein elemental sulphur is produced and a reduced sulphide-oxidising bacteria is obtained and (ii) wherein the reduced sulphide-oxidising bacteria are oxidised by transfer of electrons to an anode of an electrochemical cell to obtain the oxidised sulphide-oxidising bacteria.

12 Claims, 1 Drawing Sheet

(51) Int. Cl.
    *B01D 53/84*    (2006.01)
    *B01D 53/96*    (2006.01)
    *C01B 17/02*    (2006.01)
    *C10L 3/10*     (2006.01)
    *C25B 1/00*     (2021.01)

(52) U.S. Cl.
    CPC .......... *C01B 17/0205* (2013.01); *C10L 3/103* (2013.01); *C25B 1/00* (2013.01); *C10L 2290/26* (2013.01); *C10L 2290/541* (2013.01)

(58) Field of Classification Search
    CPC .......... C10L 2290/541; C10L 2290/26; C01B 17/0205
    See application file for complete search history.

(56) References Cited

FOREIGN PATENT DOCUMENTS

| | | | |
|---|---|---|---|
| EP | 3034157 A1 | 6/2016 | |
| WO | 2009101090 A1 | 8/2009 | |
| WO | WO-2012011984 A1 * | 1/2012 | ............. C02F 3/005 |
| WO | 2015/114069 A1 | 8/2015 | |

OTHER PUBLICATIONS

Blazquez et al. Treatment of high-strength sulfate wastewater using an autotrophic biocathode in view of elemental sulfur recovery. Water Research (Sep. 2016), 105, 395-405 (Year: 2016).*

Auguet et al. Implications of Downstream Nitrate Dosage in anaerobic sewers to control sulfide and methane emissions. Water Research (2015), 68, 522-532. (Year: 2015).*

DATABASE WPI Week 200834 Thomson Scientific, London, GB; AN 2008-E93704 XP002773263, & JP 2008094985 A (Mitsui Eng & Shipbuilding Co Ltd) Apr. 24, 2008 (Apr. 24, 2008) abstract.

DataBase WPI, Week 201631, Thomson Scientific, London, GB; AN 2016-00314G; Dec. 23, 2015 abstract.

* cited by examiner

PROCESS TO PREPARE ELEMENTAL SULPHUR

CROSS-REFERENCE TO RELATED APPLICATIONS

This application is a 35 U.S.C. § 371 National Phase Entry Application of International Application No. PCT/EP2018/064150 filed May 30, 2018, which designates the U.S. and claims benefit under 35 U.S.C. § 119(a) of EP Provisional Application 17173887.5 filed Jun. 1, 2017, the contents of which are incorporated herein by reference in their entireties.

Figure 1:
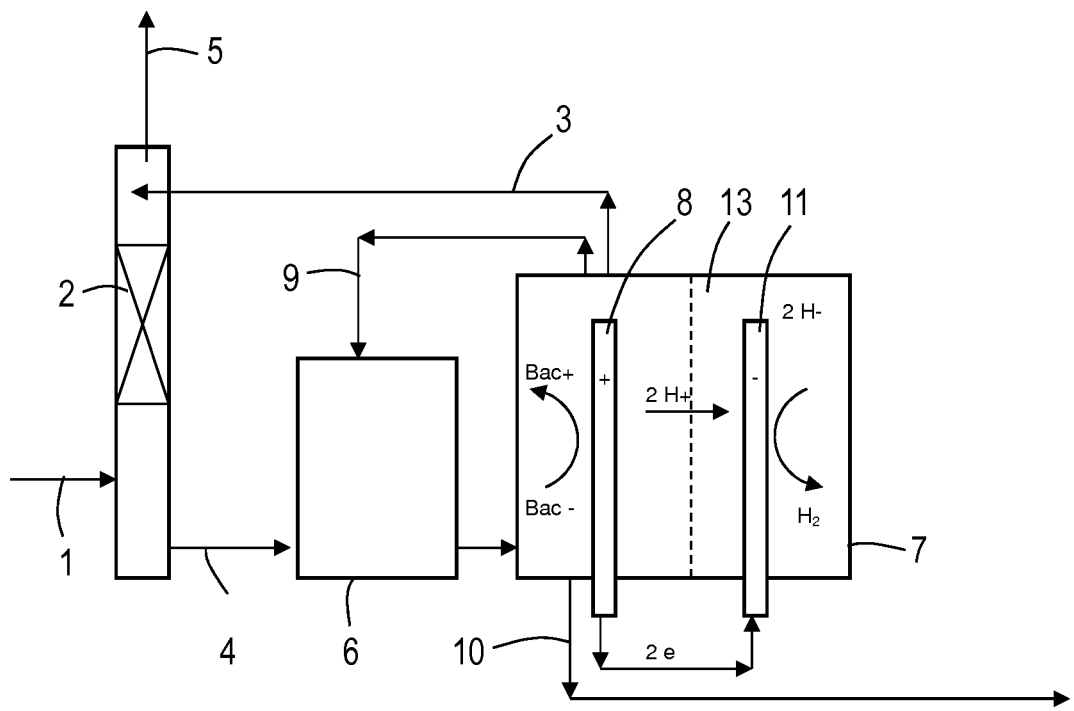
FIG. 1 shows a system in which the process of this invention can be performed.

The invention is directed to a process to prepare elemental sulphur by contacting an aqueous solution comprising bisulphide with oxidised sulphide-oxidising bacteria under anaerobic conditions wherein elemental sulphur is produced and a reduced sulphide-oxidising bacteria is obtained.

Such a process is described in WO2015/114069. In this publication a process is disclosed wherein in a first step an aqueous solution comprising bisulphide is contacted with oxidised sulphide-oxidising bacteria under anaerobic conditions. In a second step the reduced sulphide-oxidising bacteria are regenerated by contacting the bacteria with oxygen. The thus regenerated bacteria are then re-used in the first step. Elemental sulphur is isolated by sedimentation from part of the aqueous solution obtained in the second step. The thus obtained aqueous solution poor in elemental sulphur is recycled to the second step.

In the above process most of the bisulphide compounds will be converted in the first step. This is advantageous because less bisulphide will then be able to chemically react with molecular oxygen in the second step. In this manner a significant reduction of the formation of thiosulphate is achieved as compared to process which did not have the anaerobic first step. Although the formation of thiosulphate is low there is still room for improvement.

CN105176614 describes a process to catalytically oxidize hydrogen sulphide to functional microbial sulphate in the presence of a biofilm of *Desulfobulbusor Thiobacillus* present on the anode of an electrochemical cell.

The object of the present invention is to provide a process which has a low formation of thiosulphate.

This object is achieved by the following process. A process to prepare elemental sulphur by (i) contacting an aqueous solution comprising bisulphide with oxidised sulphide-oxidising bacteria under anaerobic conditions wherein elemental sulphur is produced and a reduced sulphide-oxidising bacteria is obtained and (ii) wherein the reduced sulphide-oxidising bacteria are oxidised by transfer of electrons to an anode of an electrochemical cell to obtain the oxidised sulphide-oxidising bacteria.

Applicants found that the regeneration of the sulphide-oxidising bacteria can be performed by transfer of electrons to an anode of an electrochemical cell to obtain the oxidised sulphide-oxidising bacteria. Such a process step does not require the presence of oxygen and therefore the chemical formation of thiosulphate can be greatly reduced. A further advantage is that foaming in the regeneration step can be eliminated or reduced. In the prior art process air is typically used to provide the molecular oxygen in the regeneration step. The injection of air into the aqueous solution may cause foaming. Because no air injection is required or at least not in an amount as in the prior art process the formation of foam can be reduced. Furthermore the process of regeneration of the sulphide-oxidising bacteria can be controlled in an improved manner when compared to the regeneration using a direct contacting with molecular oxygen.

When an aqueous solution comprising bisulphide is contacted with oxidised sulphide-oxidising bacteria under anaerobic conditions according to the invention oxidation of bisulphide to elemental sulfur takes place which may be described by:

$$HS^- + bac^+ \rightarrow \tfrac{1}{8}S_8 + H^+ + bac^- \quad (1)$$

Here, back is an oxidized sulphide-oxidising bacteria. While the bisulfide compound is oxidized, the bacteria is reduced or at least has taken up reduced components in a 2-electron reaction thereby obtaining $bac^-$. Molecular oxygen is typically supplied to the bioreactor in the prior art process to regenerate the bacteria. The reduction of oxygen is given by:

$$\tfrac{1}{2}O_2 + 2e^- + 2H^+ \rightarrow H_2O \quad (2)$$

In the process according to the invention the reduced bacteria ($bac^-$) transfer electrons to an anode in an electrochemical cell to obtain the oxidised sulphide-oxidising bacteria. This electrochemical anode reaction is given by:

$$bac^- \rightarrow bac^+ + 2e^- \quad (3)$$

In the process according to the invention the electrons as supplied by the reduced sulphide-oxidising bacteria are not directly transferred to oxygen. Instead the electrons are transferred to an anode of an electrochemical cell. The material of the anode may be any conductive material, for example stainless steel or titanium optionally provided with a metal coating. A preferred anode are graphite or carbon-based electrodes.

Such an electrochemical cell will also comprise of a cathode wherein the electrons as released at the anode are used to reduce another counter compound. If such a counter compound has a more positive electrode potential than the electrode potential of the reduced sulphide-oxidising bacteria an electric current between the anode and the cathode results and electric power may be produced. If the counter compound has a more negative electrode potential than the electrode potential of the reduced sulphide-oxidising bacteria the required transfer of electrons and resulting electric current between said electrodes is achieved by applying an electric potential difference between the anode and cathode. In a so-called three electrode cell, an anode potential of between −0.6 V to 0.4 V versus a Ag/AgCl reference electrode may be applied. The choice for the anode potential will depend on the desired selectivity of the process. Lower potentials will as a rule result in a more selective process and higher potentials will result in processes having a higher conversion rate wherein also more chemical conversion to sulphates may take place.

The anode and cathode may be present in the same space, more specifically in the same vessel, wherein the sulphide-oxidising bacteria may also contact the cathode. Preferably the space in which the anode is present is separated from the space in which the cathode is present by a semi-permeable membrane. Such a membrane may be an ion-selective membrane for transport of cations from anode to cathode. Such cations may be any cation which is present in higher concentrations. Examples of cations are $H^+$ and $Na^+$. The membrane may also be an ion-selective membrane for transport of anions from cathode to anode. Examples of anions are OH⁻ and $SO_4^{2-}$.

In a first preferred embodiment the electrochemical cell comprises a cathode which transfers electrons to a compound having a higher electrode potential than the electrode potential of the reduced sulphide-oxidising bacteria and wherein as a result of this difference in potential between anode and cathode an electric current between said electrodes results and electric power is produced. In order to increase the reaction rate an additional potential may be applied from an external source. The compound at the cathode, i.e. the counter compound, may for example be oxygen which electrochemical reaction at the cathode may be given by:

$$\tfrac{1}{2}O_2 + 2H^+ + 2e^- \rightarrow H_2O \qquad (4)$$

Other possible counter compounds are nitrate, ferric iron ($Fe^{3+}$), copper ($Cu^{2+}$), ozone and peroxide. The reaction at the surface of the cathode may be uncatalyzed or catalyzed. The material of the cathode may be graphite-based or carbon-based (uncatalyzed) or metal-based. Examples of catalyzed cathodes are mixed metal oxide coatings containing Pt, Ir, or other noble metals, on a conductive support like titanium. Possible catalysts are Pt, Ir, Cu and microorganisms as present as a biofilm on the cathode.

In a second preferred embodiment the electrochemical cell comprises a cathode which transfers electrons to a compound having a more negative electrode potential than the electrode potential of the reduced sulphide-oxidising bacteria and wherein an electric potential is applied between anode and cathode such that the transfer of electrons can take place. In this embodiment an electric current is generated between said electrodes, for which power input is required. The advantage of this second option is that higher rates can be achieved by increasing the applied electric potential.

Possible counter compounds having a more negative electrode potential than the electrode potential of the reduced sulphide-oxidising bacteria are for example, hydronium ions. A preferred counter compound is the hydronium ion which allows the production of hydrogen. This electrochemical cathode reaction may be given by:

$$2H^+ + 2e^- \rightarrow H_2$$

Other possible reactions which may be performed at the cathode is the reduction of hydronium ions together with $CO_2$ to methane or other chemicals like acetate, ethanol, or medium chain fatty acids. The thus produced hydrogen or methane or the hydrocarbons are useful by-products of the process according to the invention.

The contacting in (i) and the oxidation of the reduced sulphide-oxidising bacteria in (ii) may take place simultaneously in one step. By one step is here meant that the contacting in step (i) and the oxidation of the reduced sulphide-oxidising bacteria takes place in one vessel. In such an embodiment, it may be required to regenerate part of the reduced sulphide-oxidising bacteria in a separate vessel.

Preferably the contacting in (i) and the oxidation of the reduced sulphide-oxidising bacteria in (ii) may alternatively take place in separate steps. By separate steps is here meant that the contacting in step (i) and the oxidation of the reduced sulphide-oxidising bacteria takes place in two separate steps and consequently in at least two separate vessels or reactors. Although in such a process a large part of the conversion of bisulphide by the oxidised sulphide-oxidising bacteria will take place in a first step it cannot be excluded that part of the reaction will also take place when the reduced sulphide-oxidising bacteria are oxidised in (ii).

The reduced sulphide-oxidising bacteria are oxidised by transfer of electrons to an anode of an electrochemical cell to obtain the oxidised sulphide-oxidising bacteria. The electrochemical cell may be any cell which comprises an anode and cathode as described above. The anode and cathode may be present as flat plates or as co-axial tubular parts as present in a vessel. The anode and cathode may also be comprised in a single tubular part wherein preferably the anode is present at its exterior and the cathode is present at its interior. One or more of such tubes may be placed such that the anode at its exterior may contact the reduced sulphide-oxidising bacteria. Through the tube another solution may flow comprising the compound which will perform the earlier referred to electrochemical reaction at the cathode. It may even be envisaged to position such tubes in a gas scrubber in which a hydrogen sulphide comprising gas is contacted with an aqueous solution comprising oxidised sulphide-oxidising bacteria. In such a scrubber any reduced sulphide-oxidising bacteria can be in-situ regenerated, thereby obtaining a loaded aqueous solution comprising bisulphide and oxidised sulphide-oxidising bacteria and a gas having a lower content of hydrogen sulphide, If a desired degree of regeneration of the sulphide-oxidising bacteria is not obtained in (ii) it may be advantageous to oxidize the remaining reduced sulphide-oxidising bacteria by direct contacting with, for example, oxygen or nitrate. Although some of the advantages of the invention will then be less it still results in a process which overall does not have the high chemical thiosulphate and biological sulphate production as in the prior art process and which may recover energy. Thus suitably part of the reduced sulphide-oxidising bacteria are oxidised by transfer of electrons to an anode of an electrochemical cell to obtain the oxidised sulphide-oxidising bacteria and another part of the reduced sulphide oxidising bacteria are oxidised directly by contacting the reduced sulphide oxidising bacteria with oxygen or nitrate such to achieve a desired degree of regeneration of the sulphide-oxidising bacteria.

The aqueous solution of bisulphide may be dissolved hydrogen sulphide in an aqueous solution. The hydrogen sulphide is predominantly in the form of bisulphide and some sulphide, polysulphide and/or dissolved hydrogen sulphide. The aqueous solution may for example be a spent caustic solution or an alkaline absorbing solution used for absorbing hydrogen sulphide or other reduced sulphur compounds from a sour gas stream. Alternatively, the aqueous solution comprising bisulphide may be a bisulphide solution obtained by dissolving hydrogen sulphide from a highly concentrated or essentially pure hydrogen sulphide gas into an aqueous solution by means of an ejector.

Preferably, the aqueous solution comprising bisulphide is a liquid alkaline absorbent comprising bisulphide obtained in the treatment of a sour gas stream. The aqueous solution is suitably obtained by counter-currently contacting a gas stream comprising sulphur compounds including hydrogen sulphide with the liquid alkaline absorbent in an absorption column. Preferably the liquid alkaline absorbent comprises oxidised sulphide-oxidising bacteria as obtained in step (ii). Because the oxidised sulphide-oxidising bacteria take up and/or oxidize the dissolved bisulphide, a larger driving force results for the absorption of hydrogen sulphide into an aqueous solution comprising such oxidised sulphide-oxidising bacteria. The absorption is suitably performed under anaerobic conditions. The sour gas thus preferably does not contain oxygen in any significant amount. If these bacteria are present as part of the alkaline absorbent the contacting (i) may already take place during absorption.

The bisulphide concentration in the aqueous solution in (i) is not critical. Solutions with bisulphide concentrations (expressed as sulphur) as high as 20 grams per litre or even higher may be used. In such a calculation also the sulphur which has been taken up by the sulphide-oxidising bacteria is included. Preferably, the bisulphide concentration in the aqueous solution is in the range of from 100 mg/L to 15 g/L, more preferably of from 150 mg/L to 10 g/L.

The contacting (i) of the aqueous solution comprising bisulphide with oxidised sulphide-oxidising bacteria is performed under anaerobic conditions. With anaerobic conditions is meant in the absence of molecular oxygen. No molecular oxygen is supplied and/or present during such contacting. Preferably such contacting is performed in the absence of other oxidants such as nitrate. Anaerobic conditions is here meant 'in the absence of molecular oxygen' wherein the concentration of molecular oxygen in the aqueous solution is at most 1 µM, more preferably at most 0.1 µM.

The sulphide-oxidising bacteria may be any sulphide-oxidising bacteria, preferably the sulphide-oxidising bacteria is of one of the following strains: *Halothiobacillus, Thioalkalimicrobium, Thioalkalispira, Thioalkalibacter, Thioalkalivibrio, Alkalilimnicola* and related bacteria. These haloalkaliphilic sulfide-oxidising bacteria are suited for this process.

The bacteria may be used as such, i.e. may be present as planktonic cells the aqueous solution or may be supported on a dispersed carrier.

The contacting (i) of the aqueous solution comprising bisulphide with oxidised sulphide-oxidising bacteria may take place at any suitable conditions of temperature, pressure and hydraulic residence time suited for performing the biological oxidation of bisulphide into elemental sulphur. Preferably the temperature is in the range of from 10 to 60° C., more preferably of from 20 to 40° C. The pressure is suitably in the range of from 0 bara to 100 bara, more preferably of from atmospheric pressure to 80 bara. The pH of the aqueous solution is suitably in the range of from 7 to 10, more preferably in the range of from 7.5 to 9.5. The salinity of the aqueous solution as expressed as molar concentration of cations, and preferably molar concentration of total cations of sodium and/or potassium, is preferably between 0.3 and 4 M and more preferably between 0.5 and 1.5 M. The aqueous solution may comprise trace compounds of several different compounds, such as for example iron, copper or zinc, as nutrients for the sulphide-oxidising bacteria. The residence time in case of a continuous process or contact time in case of a batch process is preferably at least 3 minutes, more preferably at least 5 minutes, more preferably at least 10 minutes. The maximum residence time is not critical, but for practical reasons, the residence time is preferably at most 2 hours, more preferably at most 1 hour.

Preferably the weight ratio of nitrogen as part of the total of the sulphide-oxidising bacteria and total amount of bisulphide is at least 0.1 mg N/mg bisulphide, preferably at least 0.5 mg N/mg bisulphide, more preferably at least 0.7 mg N/mg bisulphide.

The aqueous solution which comprises reduced sulphide-oxidising bacteria as obtained in (i) when the aqueous solution comprising bisulphide is contacted with oxidised sulphide-oxidising bacteria will also comprise elemental sulphur. Elemental sulphur may be separated from the aqueous solution before, during or after the oxidation of the reduced sulphide-oxidising bacteria in (ii). The elemental sulphur may also deposit on the anode. The deposited elemental sulphur can be simply separated from the anode, optionally in the absence of the aqueous solution.

The invention may also be advantageously used to improve existing processes which convert sulphides to elemental sulphur by making use of oxidised sulphide-oxidising bacteria. In such know processes the regeneration of the used and thus reduced sulphide-oxidising bacteria is typically performed by contacting the reduced oxidised sulphide-oxidising bacteria with molecular oxygen. The sulphides are typically absorbed by contacting the hydrogen sulphide comprising gas with an aqueous solution comprising oxidised sulphide-oxidising bacteria. This absorption step is also described below. The aqueous solution used in this absorption is prepared in the regeneration step. It is found that the aqueous solution may still contain some reduced sulphide-oxidising bacteria. By oxidising these remaining reduced sulphide-oxidising bacteria prior to using this solution in the absorption step by transfer of electrons to an anode of an electrochemical cell as described above an aqueous solution is obtained containing a higher level of oxidised sulphide-oxidising bacteria. It is found that such a solution can more effectively absorb hydrogen sulphides. Such an additional step involving transfer of electrons to an anode of an electrochemical cell can be easily added to existing processes. Therefore the invention is also directed to a process to improve the effectiveness to absorb hydrogen sulphide of an aqueous solution comprising oxidised and reduced sulphide-oxidising bacteria in a hydrogen sulphide absorption process by oxidising the reduced sulphide-oxidising bacteria by transfer of electrons to an anode of an electrochemical cell.

The above described process may also be preferably performed as part of a process to treat a hydrogen sulphide comprising gas as described below. The invention is thus also directed to a process to treat a hydrogen sulphide comprising gas comprising the following steps:
  (a) contacting the hydrogen sulphide comprising gas with an aqueous solution comprising oxidised sulphide-oxidising bacteria thereby obtaining a loaded aqueous solution comprising bisulphide and oxidised sulphide-oxidising bacteria and a gas having a lower content of hydrogen sulphide,
  (b) contacting the loaded aqueous solution comprising bisulphide with oxidised sulphide-oxidising bacteria under anaerobic conditions wherein elemental sulphur is produced and a reduced sulphide-oxidising bacteria is obtained, and
  (c) oxidising the reduced sulphide-oxidising bacteria by transfer of electrons to an anode of an electrochemical cell to obtain the oxidised sulphide-oxidising bacteria for reuse in steps (a) and
  (d) isolating elemental sulphur from the aqueous solution obtained in any of steps (a)-(c).

Step (a) may be performed by well-known processes for absorption of bisulphide. The gas temperature may be in the range of from 0° C. to 100° C., preferably of from 20° C. to 80° C., more preferably of from 25° C. to 50° C. and a pressure in the range of from 0 bara to 100 bara, preferably of from atmospheric pressure to 80 bara. The liquid alkaline absorbent may be any liquid alkaline absorbent known to be suitable for absorption of hydrogen sulphide, i.e. known to dissolve sulphides. Examples of suitable liquid alkaline absorbents are carbonate, bicarbonate and/or phosphate solutions, more preferably a buffered solution comprising carbonate and bicarbonate. Buffered solutions comprising sodium or potassium carbonate and bicarbonate are particularly preferred, more in particular a buffered solution comprising sodium carbonate and sodium bicarbonate. The pH of the liquid alkaline absorbent that is supplied to the upper part of the absorption column, is preferably in the range of from 7 to 10, more preferably of from 7.5 to 9.5.

Preferably such an absorption is performed in an absorption column wherein the hydrogen sulphide comprising gas stream is contacted in the absorption column with all or preferably part of a liquid effluent as obtained in step (c). Step (a) is preferably performed under anaerobic conditions and some elemental sulphur and reduced sulphide-oxidising bacteria may also be obtained while performing step (a). In step (b) a liquid effluent containing reduced sulphide-oxidising bacteria may be obtained which liquid effluent is oxidised in step (c). Part of the liquid effluent as obtained in step (c) is recycled to step (b). The liquid effluent of step (c) may before being recycled to the absorption column and/or to step (b), be subjected to step (d). Part of the effluent poor in elemental sulphur as obtained in step (d) may be purged. Preferably elemental sulphur is isolated from the aqueous solution obtained in step (c) to obtain elemental sulphur and an aqueous solution poor in elemental sulphur. This aqueous solution comprising predominately oxidised sulphide-oxidising bacteria may also contain some reduced sulphide-oxidising bacteria. In order to also oxidize as much of these remaining reduced sulphide-oxidising bacteria it is preferred to oxidize in a separate step (e) the reduced sulphide-oxidising bacteria by transfer of electrons to an anode of an electrochemical cell before using this aqueous solution in step (a).

Preferably steps (b), (c) and (e) are performed as described for the process according to the present invention as described above.

The invention will be illustrated by FIG. 1. FIG. 1 shows a hydrogen sulphide comprising natural gas (1) being contacted in an absorption column (2) with an alkaline aqueous solution comprising oxidised sulphide-oxidising bacteria (bac$^+$) as fed via stream (3) to the upper end of column (2). A loaded aqueous solution (4) comprising bisulphide and oxidised and reduced sulphide-oxidising bacteria (bac$^+$/bac$^-$) is obtained as a bottom stream and a natural gas (5) having a lower content of hydrogen sulphide is obtained as a top stream effluent of the column. The loaded aqueous solution is fed to an anaerobic reactor (6) and subsequently to electrochemical cell (7). In anaerobic reactor (6) elemental sulphur is produced and most of the oxidised sulphide-oxidising bacteria (bac$^+$) will be converted to reduced sulphide-oxidising bacteria (bac$^-$). In electrochemical cell (7) the reduced sulphide-oxidising bacteria (bac$^-$) are oxidised by transfer of electrons to an anode (8). Oxidised sulphide-oxidising bacteria (bac$^+$) are obtained. Liquid effluent as obtained at the anode side of the electrochemical cell is in part (via stream (9)) recycled to anaerobic reactor (6) and in part used as absorbent via stream (3). Aqueous solution poor in elemental sulphur may be returned to the anode side of the electrochemical cell or added to stream (9) and/or stream (3). Between anode (9) and cathode (11) an electric potential is created to drive the reaction at anode and cathode. Between the space in which the anode (9) is present and the space in which the cathode (11) is present an ion-selective membrane (13) is positioned. At cathode (11) hydrogen is prepared and discharged as stream (12). Hydrogen may in a subsequent step be reacted with carbon dioxide to prepare methane. This methane may be combined with natural gas stream (5).

From the liquid effluent as obtained at the anode side elemental sulphur (10) is isolated by sedimentation (not shown in FIG. 1). Elemental sulphur may also be isolated by sedimentation in a separate step (not shown in FIG. 1) from the aqueous solution obtained in anaerobic reactor (6) before treating the aqueous solution in electrochemical cell (7).

EXAMPLE 1

Three experiments were performed in a three electrode setup 100 ml of an aqueous solution with a biomass concentration of 80 grN/L of reduced sulphide-oxidising bacteria (bac$^-$) as obtained in an anaerobic reactor of a process as described in WO2015/114069 was contacted with a graphite rod as anode at different anode potentials of −0.1V, 0V, and 0.1V vs Ag/AgCl in a so-called three electrode set up. The sulphide-oxidising bacteria in the aqueous solution were contacted with bisulphide and most of the sulphide-oxidising bacteria were reduced sulphide-oxidising bacteria (bac$^-$).

The experiment was repeated for the medium alone. The medium was obtained by separating the bacteria from the aqueous solution by means of centrifugation at 10000 rpm for 10 min.

Figure 2:
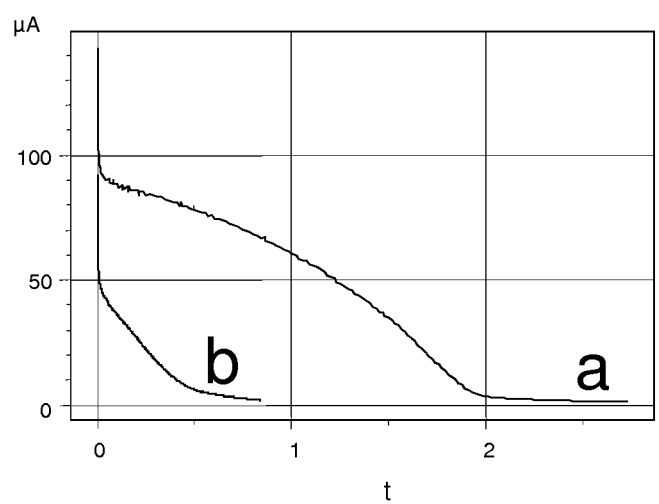
FIG. 2 shows the results for Example 1.

The result for 0.1 V vs Ag/AgCl is shown in FIG. 2. FIG. 2 shows that the aqueous solution with the sulphide-oxidising bacteria (line a) resulted in higher recovered charge than the medium alone (line b), revealing electron storage inside the sulphide-oxidising bacteria. A small current was produced from the medium alone, which may be the result of traces of bisulfide (electrochemical oxidation). The total charge that was harvested from the solution with microorganisms was 112 mC, while the same volume of medium produced only 13 mC. This means that 99 mC of charge was stored inside the sulphide-oxidising bacteria.

The invention claimed is:

1. A process to prepare elemental sulphur by
   contacting an aqueous solution comprising bisulphide with oxidised sulphide-oxidising bacteria under anaerobic conditions wherein elemental sulphur is produced and a reduced sulphide-oxidising bacteria is obtained and isolating elemental sulphur from the aqueous solution;
   wherein the reduced sulphide-oxidising bacteria are oxidised by transfer of electrons to an anode of an electrochemical cell to obtain the oxidised sulphide-oxidising bacteria; and
   wherein the electrochemical cell comprises a cathode which transfers electrons to a compound having a more positive electrode potential than the electrode potential of the reduced sulphide-oxidising bacteria and wherein as a result of this difference in potential between anode and cathode an electric current between said electrodes results.

2. The process according to claim 1, wherein the compound having a higher electrode potential than the electrode potential of the reduced sulphide-oxidising bacteria is oxygen or nitrate.

3. The process according to claim 1, wherein the electrochemical cell comprises a cathode which transfers electrons to a compound having a more negative electrode potential than the electrode potential of the reduced sulphide-oxidising bacteria and wherein a potential is provided between anode and cathode such that the transfer of electrons can take place.

4. The process according to claim 3, wherein the compound having a lower electrode potential than the electrode potential of the reduced sulphide-oxidising bacteria is the hydronium ion and wherein hydrogen is produced.

5. The process according to claim 1, wherein the contacting in (i) and the oxidation of the reduced sulphide-oxidising bacteria in (ii) take place in separate steps.

6. The process according to claim 1, wherein the anaerobic conditions are defined as a concentration of molecular oxygen in the aqueous solution of at most 0.1 µM.

7. The process according to claim 1, wherein the pH of the aqueous solution is between 7.5 and 9.5.

8. The process according to claim 1, wherein the salinity of the aqueous solution expressed as the molar concentration of the total of sodium and/or potassium cations is between 0.5 and 1.5 M.

9. The process according to claim 1, wherein in (ii) a potential of between −0.6 to 0.4 V is applied to the anode versus a Ag/AgCl reference electrode.

10. The process according to claim 1, wherein aqueous solution comprising bisulphide is obtained by contacting an alkaline absorbent with a sour gas comprising sulphur compounds including hydrogen sulphide.

11. The process according to claim 10, wherein the alkaline absorbent comprises oxidised sulphide-oxidising bacteria as obtained in step (ii).

12. The process of claim 1, wherein the sulphide oxidising bacteria are present as planktonic cells or supported on a dispersed carrier.

* * * * *